United States Patent [19]

Relyea

[11] 4,408,613

[45] Oct. 11, 1983

[54] INTERACTIVE EXERCISE DEVICE

[75] Inventor: Richard D. Relyea, Austin, Tex.

[73] Assignee: Aerobitronics, Inc., Austin, Tex.

[21] Appl. No.: 307,738

[22] Filed: Oct. 2, 1981

[51] Int. Cl.$^3$ ............................................... G01L 5/02
[52] U.S. Cl. .................................... 128/670; 128/671; 272/DIG. 5; 272/DIG. 6
[58] Field of Search ................ 73/379; 128/25 B, 363, 128/670, 671, 672, 691, 718; 272/69, 70, 72, 73, DIG. 5, DIG. 6; 364/413

[56] References Cited

U.S. PATENT DOCUMENTS

| | | | |
|---|---|---|---|
| 4,112,928 | 9/1978 | Putsch | 272/73 |
| 4,244,021 | 1/1981 | Chiles | 272/73 |
| 4,278,095 | 7/1981 | Lapeyre | 272/69 |
| 4,342,454 | 8/1982 | Baer et al. | 273/DIG. 28 |
| 4,358,105 | 11/1982 | Sweeney | 73/379 |

Primary Examiner—Richard J. Apley
Assistant Examiner—George Yanulis
Attorney, Agent, or Firm—Gunn, Lee & Jackson

[57] ABSTRACT

In the preferred and illustrated embodiments, an interactive exercise device is disclosed. One embodiment utilizes an exercise bicycle wherein wheel speed and force are monitored. An electromagnetic brake is adjusted by a control apparatus to relate the measured force to the required force. The electromagnetic brake controls the drag to implement a selected exercise program. The program paces the user through a specified load for a specified interval. The work load can be varied in any manner to achieve a desired exercise program. The interactive apparatus utilizes a video monitor to display an exercise program or race for the user. The race or exercise program is recorded on a video cassette. On playback, the cassette provides video for the monitor to be viewed by the user. The audio track is conveniently used to record instructions which are converted into a drive current for the brake, thereby modifying the drag and required velocity of the user. An alternative form is presenting exercise instructions on the video monitor via graphics or stored symbols. An alternative embodiment utilizes dead weight lifting equipment either with a linearly moved bar or a rotated shaft to provide an exercise program paced to the user.

16 Claims, 1 Drawing Figure

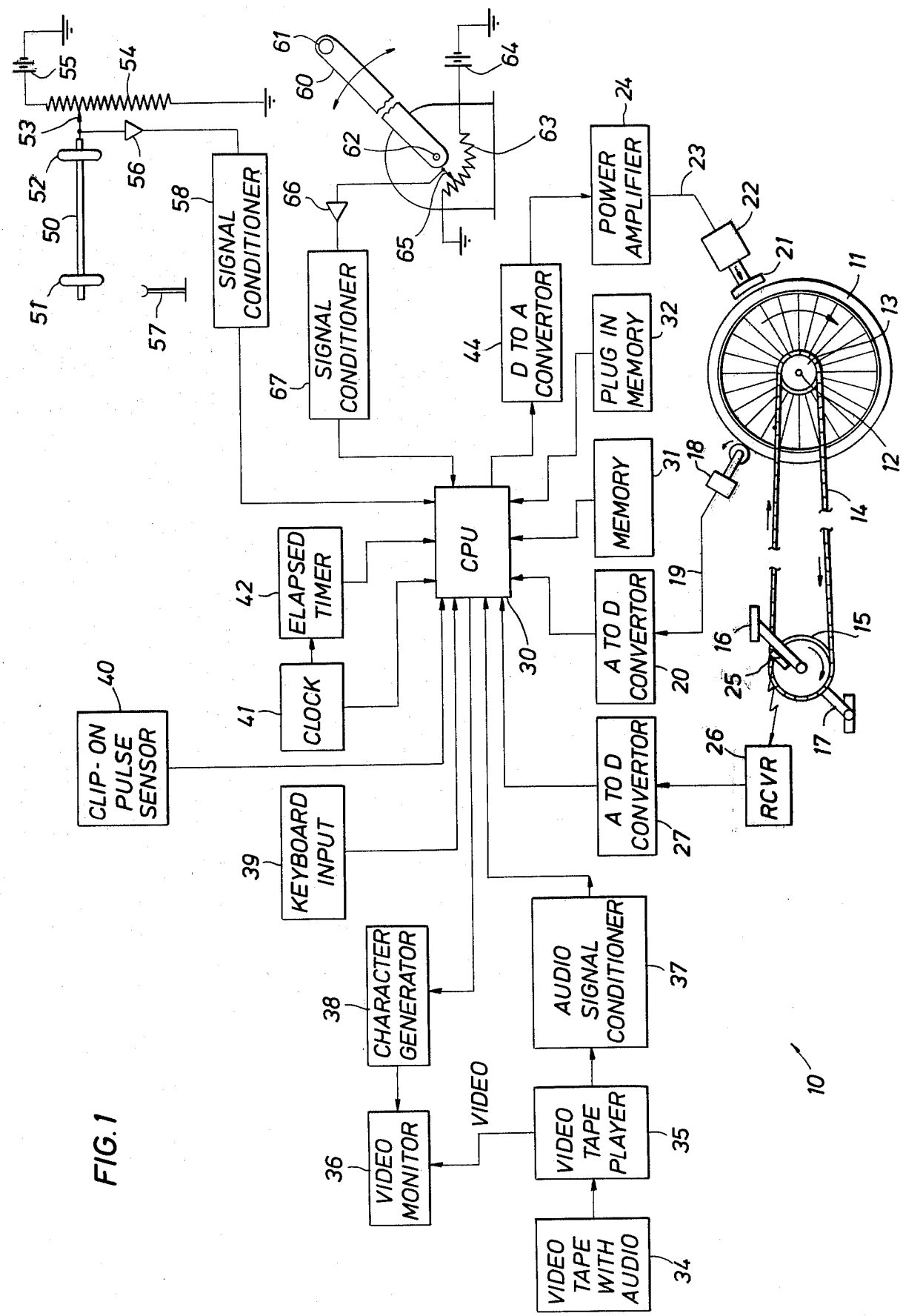

INTERACTIVE EXERCISE DEVICE

BACKGROUND OF THE DISCLOSURE

This device is directed to an exercise apparatus which cooperates interactively with the user. A program is determined for a particular user. By way of example, assume that the program is a ten minute bicycle ride. This apparatus interactively controls an exercise bicycle, the exercise bicycle being of the stationary kind, with a view of properly stressing the user. Other exercise devices are discussed below. Assume, for the moment, that the user is in rather poor shape. A ten minute exercise program, paced through a video monitor provided conveniently in view of the user, is used to pace the user. Eventually, the user becomes stronger and able to exercise at a more strenuous rate. The apparatus of this disclosure is an exercise device which modifies the load experienced by the user. Accordingly, the same exercise program is viewed again, but it is modified to thereby provide a greater strain and greater exercise to the user. This apparatus contemplates the use of a plug-in and removable read only memory (ROM) which contains the bias factor. ROMs come in various sizes. It is possible to use only one ROM containing all the exercise programs and the bias factors. Two ROMs can be used, one to store a program for exercise and the other to the bias factors or loading factors which determine the degree of difficulty of the program. The bias factor can then be selectively changed by changing the ROM periodically. This permits the user to increase the load required on the user and thereby modify the program to more vigorous levels of exercise.

It is believed that this apparatus is a marked advance over the structure found in the patent of Flavell, U.S. Pat. No. 4,184,678. Another device of interest is the patent of Dr. Wayne Book, et al, U.S. Pat. No. 4,235,437. Both patents are directed to relatively complex disclosures. As an example, the Book patent is a type of XY tracking machine for controlling the stroke of a dynamic sportsman. It is particularly intended to get the athlete into a groove, thereby enhancing his form and strength relative to the groove. It is particularly intended for use in repeated motions. It is conjectured that both of these devices are relatively expensive and comprise relatively complex structures.

One advantage of this apparatus is the ability to monitor the cardiovascular system of a patient. An important measure of fitness of a user is the cardiovascular performance of the patient or user. One parameter relating to this is oxygen uptake. This is the time rate of oxygen consumption. It is believed to be a medically sound criteria of the health and hence the condition of a user. It relates, in large part, to the heart rate, body fatigue, blood flow in the body, and other barometers of cardiovascular performance. One way to obtain this rate is to place a respirator on the user. This is an awkward piece of equipment to use. Sometimes, it is installed with a treadmill or other exercise device whereby the user is forced to breath through the respirator. Even though the respirator is a relatively clumsy device to use, it, hoever, does provide a direct measure of oxygen uptake.

It has been discovered that oxygen uptake can be inferred from other variables which are more easily obtained. This relationship is rather subtle and must be obtained by inference using this apparatus. The interactive device of this disclosure measures the heartbeat of the user and his power output applied to the exercise device. The settings on the exercise bicycle are adjusted in programmed settings to force a certain power rate from the user.

An exercise bicycle is a practical and consistent exercise device for users who have varient styles. It is highly desirable that the power rate settings be immune to variation for all users. Some exercise devices penalize certain users and reward others dependent on their style. An exercise bicycle is reasonably independent of style. In other words, good style or bad style by the user does not change the rate of exercise of the user. The exercise bicycle powered by the user establishes a power rate. Settings varied by the interactive control system require different power rates from the user. The measured power rate coupled with measurement of the pulse rate of the user during exercise enables the interactive device of this disclosure to determine the oxygen uptake. Upon applying a specified exercise regime' to the user and controlling the settings to require a specific rate of power output and measuring pulse rate during a timed interval (typically in the range of about ten minutes), the oxygen uptake can be extrapolated very accurately to thereby provide a good indication of the cardiovascular condition of the patient. The rate calculations are made using the stored data. It is fair to say that the cardiovascular system condition is indicative of the overall condition of the patient. In terms of sustaining good health, it is particularly important.

Another advantage of this apparatus is the ability of the device to adapt from one level of performance to another readily with a different user. For instance, the device can be equipped with an easily removed plug-in cartridge providing a video taped exercise program; that can be changed in a matter of seconds. It is viewed by the user who is caused to mimic the program seen by the user. Even for a given video program, the difficulty of the program can also be altered. This is a type of weighting which is manifested by altering the drag of the brake of the exercise bicycle. The device is also adapted to be used with weights which are lifted. A typical arrangement is a weighted bar which is raised and lowered relative to a set of guide tracks. An alternate form is a weight which is rotated about a pivot point.

Other advantages of this apparatus will be noted upon the detailed description of the disclosed apparatus.

BRIEF DESCRIPTION OF THE APPARATUS

This apparatus is an interactive exercise device. The exercise device preferably has the form of an exercise bicycle. A second form is a weighed bar, typically a barbell or a loaded rotatable shaft and lever. The device utilizes a video monitor, and a video tape cassette is plugged into a video tape player to provide a visual program for the video monitor. An alternate visual image is formed from encoded graphics with or without text. In this mode, the displayed images are stored in the memory and output to the video monitor under control of the CPU. Thus, no video tape recorder is required in this mode. The user is positioned where the video monitor can be viewed, and the user attempts to mimic the video monitor. The exercise device is dynamically controlled by means of a brake. The brake is driven by a power amplifier which amplifies a signal from a digital to analog converter. The digital control signals originate with a program input to a central processing unit.

Elapsed distance or mileage on the bicycle wheel is measured. This enables the user to be paced through a program of specific distance and/or time.

BRIEF DESCRIPTION OF THE DRAWINGS

So that the manner in which the above recited features, advantages and objects of the invention, as well as others, which will become apparent, are attained and can be understood in detail, a more particular description of the invention, briefly summarized above, may be had by reference to the embodiments thereof illustrated in the appended drawings, which drawings form a part of this specification. It is to be noted, however, that the appended drawings illustrate only typical embodiments of the invention and are not to be considered limiting of its scope, for the invention may admit to other equally effective embodiments.

FIG. 1 is a schematic block diagram of the interactive exercise apparatus of the present invention incorporating alternate exercise devices.

DETAILED DESCRIPTION OF THE PREFERRED EMBODIMENT

Attention is first directed to FIG. 1 of the drawings. The interaction exercise device is identified generally by the numeral 10. It is cooperative with a stationary exercise bicycle in one embodiment. This will be described first. The exercise bicycle includes a rotatable wheel 11. The wheel 11 is rotated around a fixed axle 12. The axle 12 supports a driven sprocket 13 which is powered by a bicycle chain 14. The stationary bicycle includes a larger sprocket 15 for driving the chain 14. The sprocket 15 includes conventional pedals 16 supported on crank arms 17. The equipment described to this juncture is the equipment normally found in a stationary exercise bicycle having a seat for the user, a pair of pedals adapted to receive the user's feet, and a rotatable wheel.

This apparatus is modified to include a displacement pickup 18. This forms a signal on a conductor 19 supplied to an analog to digital converter 20. The signal is accumulated to yield distance directly and can be differentiated to yield velocity. The pickup 18 is mounted on the stationary axle 12 or at the periphery of the wheel. Any arrangement of this sort is acceptable. The device also cooperates with a dynamic brake 21. The brake 21 is typically a friction brake which engages the wheel. The friction brake can be of any known construction which is electromagnetically powered by a variable force coil or solenoid mechanism 22. The brake contacts against the wheel. Alternatively, a pincer or clamp mechanism can be used. Whatever the case, the braking force is approximately proportional to the power applied to the solenoid powered mechanism 22. This, in turn, is applied through a conductor 23 from a power amplifier 24. The system can be calibrated so that output force is known from this output current which is controlled by the CPU (to be described). The braking force is approximately proportional to the current from the amplifier 24. One alternative form for measuring force involves mounting a clamping brake on the frame by a spring. On braking, the brake is pulled along with the wheel and stretches the spring. The spring elongation is proportional to force and deflection indicates the extent of braking force. The force is easily measured because the deflection distance is proportional to an easily measured current.

Another variable which is measured is the force applied by the user. There are several ways to measure this. One is to mount a resistance wire strain gauge on the crank throw. To this end, the numeral 25 identifies a resistance wire strain gauge mounted on the crank throw. As force is applied to the crank throw, a bending torque is created, and this torque is measured by the strain gauge. The strain gauge signal is transferred to a receiver 26. In the preferred embodiment, a small transmitter transmits to the receiver 26. An alternate arrangement is to utilize a commutator. In either case, the strain gauge signal is measured and transferred. The strain gauge signal is then supplied to another analog to digital converter 27 which forms an output indicative of the momentary or instantaneous force in the crank.

It will be observed that three variables are measured. In all cases, it is not essential to have all three values. For instance, the pedal torque can be omitted, and measurements of the braking force (roughly proportional to the current), as well as the elapsed mileage or distance measured by the displacement pick off will suffice. It will be appreciated that the distance is cumulative over a period of time. Accordingly, the first derivative of this value is velocity, and the second derivative is acceleration. Therefore, all three of these variables can be obtained through time dependent differentiation of this signal. Signal differentiation is accomplished by known programs. The several values (distance, velocity and acceleration as needed) are stored in the form of sequential samples at a specified sample rate.

The operative state of the bicycle is determined instantaneously during use. These signals are provided for subsequent manipulation. They are delivered to a central processing unit (CPU) 30. The CPU is ideally a microprocessor unit. The term CPU, hereinafter, refers to any capacity and any size CPU including microprocessors. Representative devices include the Z80 and 6800 family of microprocessors. The CPU has an input from a memory 31. This is a memory suitable for receiving and storing the program for the device. A second memory is identified at 32. This is a plug-in memory. It has the preferred form of a cartridge containing ROM memory. Ideally, it is permanent memory. To this extent, it can be a grid of diodes which are selectively burned to store permanent values in memory. It is a set of weighting factors. The several weighting factors are stored for the express purpose of operating the bicycle or other exercise device with specified bias levels in its operation. Moreover, the exercise bicycle can be weighted so that the program to be implemented (described hereinbelow) is weighted with different values of difficulty. For instance, one value can be the weighting of grade measurements. As the device will be described, the bicycle rider will go upgrade as the user mimics the program. This interplay will be described below. The ROM 32 is typically two separate plugin cartridges. One stores a program for the exercise. The second ROM stores the weighting factors. A given ROM program may have, for example, one hundred factors stored in the second ROM. The stored factors are easily changed by removing the second ROM and replacing it with an alternate ROM. Of course, a single ROM may be used if large enough.

A video tape with an audio track is identified at 34. It is played through a typical video tape player 35. It provides two outputs, one being video and the other being audio. The video output is provided to a video monitor 36. Ideally, the video monitor is installed close to and within the field of vision of the user using the exercise bicycle. The video monitor is preferably a fairly large screen television monitor, even in color. It serves to interactively engage the user during exercise programs. An alternate form is a typical TV set capable of black and white or color images.

The video tape cassettes are recorded with certain audio signals thereon. They are transferred through the video tape player to an audio signal conditioner 37. The audio signals are, in turn, transferred to the CPU 30 in the form of digital instructions for the CPU. The CPU has an additional output which is signals applied to a character generator 38. A keyboard 39 inputs instructions as desired. They may be in memory or input by hand. The character generator forms output signals for the video monitor 36. Also, the character generator can form graphic symbols, slogans, charts and the like. The symbol can be used to form animated characters, bicycles, scenery and the like similar to those from games of various manufacturers. Alternatively, a microcomputer chip may be used in lieu of a CPU and separate memory. A microcomputer is a device in which the microprocessor and memory (RAM and/or ROM) are integrated onto a single integrated circuit chip.

The device incorporates a clip-on pulse sensor 40. This is attached to the skin of the user to measure the pulse rate of the user. The blood vessel system of the user is close to the surface at several locations on the body where the pulse can be observed. Obviously, it can be observed in the wrist or on the neck. Another location is the earlobe, finger, throat or chest areas. Whatever the case, a transducer is utilized which is responsive to the pulsations of the cardiovascular system of the user and signals are formed which are input to the CPU 30 indicative of the pulse rate. In addition, the device cooperates with a system clock 41. The clock drives an elapsed timer 42. The elapsed time and pulse sensor signals are input to the CPU. The pulse rate is easily calculated from pulse sensor signals.

The CPU drives the character generator 38 to place certain symbols on the screen. These may be words, texts, comparative charts, or any other symbol. In addition, the CPU drives a digital to analog converter 44. This device, in turn, provides an analog signal to the power amplifier 24 which is amplified. It forms a braking force which is proportional to the signal from the converter 44.

Certain components for use with dead weights are also shown in FIG. 1. They will be described after a sequence of operation with the exercise bicycle has first been described.

DESCRIPTION OF OPERATION

Assume, as an initial condition that a video tape has been provided which has ten minutes of play time. Assume further, that this video tape has been recorded by a bicycle rider traveling along a path which is divided into four segments. Assume further, for ease of description, that the ten minute trip has been divided into the following four segments, namely travel of 1,000 feet on level ground, 1,000 feet up an incline with a 2% grade, another 1,000 feet down an incline with a 2% grade and 7,480 feet which is level. This is a total of two miles, and if covered in ten minutes, corresponds to a speed of twelve miles per hour. On the video portion of the video tape 34, a camera mounted on a bicycle traveling along this path records that path dynamically as seen by the bicycle rider. That is played through the monitor 36 and is observed by the user. The user is able to follow the action visually and is inevitably drawn into participation with the scene that is flashed on the video monitor 36. So to speak, the user becomes a part of the scene. Realism of the scene is an enhancing factor to the activity of the user on the exercise bicycle.

Consider the first segment of the ride which is stored on video tape at 34. It corresponds to a level ride of 1,000 feet at an average speed of twelve miles per hour. This, in turn, corresponds to a certain wind resistance and mechanical drag of the apparatus. This resistance is simulated for the user by adjusting the position of the brake 21. The drag which is created on level ground at twelve miles per hour is a known quantity. To this end, a specific signal is applied to the brake 21. This signal is recorded in the form of audio information on the video tape 34. It is separated by the video tape player 35 which, in turn, transfers the audio information to the signal conditioner 37. It forms a coded signal which is transferred to the CPU. This signal corresponds to a specific brake drag, and that might be defined as a 25% setting on the brake. The brake is then provided with a control signal. This is formed by converting the digital signal into an analog signal through the converter 34, applying that to the amplifier 24, and operating the solenoid 22, thereby forming a 25% drag factor on the brake. This drag factor is applied for the duration of the trip on the 2% grade. This distance is measured and summed to indicate the elapsed distance and initiates the next exercise required of the user.

Assume that the bicycle rider is traveling more rapidly than the program permits for the user. This would cover 1,000 feet more rapidly than the film. The speed and elapsed travel distance of the user is independent of speed evidenced on the film. However, timed events on the film should be met by the user to keep up with the sequence of filmed events. The goal, in using the film, is to become visually linked to the film so that each programmed step is controlled. The odometer 18 is operated to form an output indicative of position and velocity. The CPU responds to these inputs (velocity, force and distance) to compute simulated distance against grade, simulated work, or any other variable of interest. As an example, work is given by the force times distance and the CPU can readily determine this value as a performance measure.

If the velocity is too great compared with a programmed goal, the user will cover the simulated 1,000 feet too rapidly. The user is, therefore, slowed by instructions to the brake. If the rate of operation by the user is excessive, the drag of the brake is increased dynamically to slow the user. The user is thus slowed to the desired rate. This slowing manifests itself to the user by increased drag. The user, in turn, responds to this by pedalling more slowly which reduces the drag. The drag is reduced until the user is able to maintain a constant and desired drag indicative of the mimicked bicycle trip evidenced on the video monitor. One alternate use would be to use the speed as a variable in conjunction with the measured force to yield a measured calculation of work. An important feature is that with this device, a number of ways to exercise is possible merely by using different programs which are plug-in ROMs. One major advantage is that the user does not get bored since he is busy watching the scenery, etc. of a simulated bike ride.

At the second segment, the user is then required to travel 1,000 feet up a 2% grade. A 2% grade might correspond to a drag setting of 40% on the brake. Accordingly, the audio portion of the video tape is used to encode signals indicative of the change in velocity (if any) and the change in grade, and in this instance, that is assumed to be 2%. This change in grade is sustained for a programmed interval. The 1,000 foot duration is viewed on the video monitor dynamically. The video monitor shows the scenery which is inherently tied to an upgrade condition. This scenery continues until the 1,000 foot distance has been covered.

During this upgrade ride, the user experiences a brake drag of 40% scaled to correspond to the simulated grade. If the user overspeeds, the brake drag can be increased from 40% to a higher percentage level as, for instance, 50% or 60%. This encourages the user to drop his speed to the calculated average speed for the trip.

On the downgrade condition, the distance and grade are signalled by audio content on the video tape 34. The audio signals are separated and applied to the CPU. The downgrade condition is simulated by changing the setting on the brake drag to perhaps 15% to simulate the downgrade operation. The fourth condition is travel through 7,480 feet on a horizontal grade. This, again, is indicated to the user by setting the drag brake at the 25% position. Again, the simulated distance is measured by the odometer 18.

In the foregoing, it will be observed that the user is instructed dynamically in pedalling by the setting of the drag brake. The user experiences the same trip that was experienced by the video tape recording camera mounted on a bicycle which originally recorded the video tape 34. So to speak, the cameraman plans the trip for the user. Restated, a particular trip can be tailor-made by the cameraman.

In the foregoing, it was presumed that the user would attain the speed of the mimicked or video tape recorded trip. Alternatively, the user might exceed that speed, and the drag of the brake would be adjusted to slow down the user. In the event the user goes too slow, this can be determined by comparing the rate of speed of the user as measured by the velocity detector 18 with the required or desired rate. Should the user fall perhaps as much as 3% or 4% below the rate required to maintain the recorded pace, this can be signaled to the user by forming an instruction to this effect which is relayed to the character generator 38 which, in turn, flashes a signal on the screen of the video monitor 36. To this end, a few simple instructions (speed up, slow down and hold your speed) will aid the user in setting a pace. These would be flashed on the screen to be viewed by the user. The system can, however, switch the video from the VCR to the CPU to allow a message to be displayed from the CPU, and then switch back to the VCR.

The foregoing presumes that the user travels on the exercise bicycle at a rate of speed which is exacty equal to that recorded on the video tape 34. The matching of speed is not required in use. In fact, speed of a bicycle normally requires information on the gear ratio and tire size. Accordingly, drag of the exercise bicycle and speed will simulate without duplicating the drag of the bicycle in use. The program imposes a specific load on the user. It is, however, possible to bias the load experienced by the user. To this end, the plug-in memory 32 incorporates many optional ROMs. Each can store a set of bias instructions. The loading experienced by the user can, therefore, be weighted to different levels for the entire simulated trip. The foregoing bicycle trip can be described as a standard trip. It can be reduced in load for an older user, as for instance, by reducing the drag factor(s) in the stated example by 25%. This drag factor can be reduced across the entire program of all segments of the user's trip. The weighting factor is thus stored in the plug-in memory 32 and reduces all values of brake setting by 25%. Conversely, for a very strong and healthy individual, the plug-in memory 32 might be substituted and a very difficult and arduous bicycle trip can be planned. All weighting factors could be increased by perhaps 50%. This would clearly increase the strain experienced by the user to those levels appropriate for a younger and relatively healthy user. In like fashion, the hills can be made more severe or less severe. Moreover, the required velocity or speed of the bicycle can be changed. For instance, the original example wherein the brake was set at 25% resistance for level travel can be maintained while the speed required, as measured by the displacement pickup 18 can be adjusted from twelve miles per hour to sixteen miles per hour. This scale factor is stored in the plug-in memory 32. The plug-in memory 32 can thus hold scale factors requiring the user to maintain 100% of the values stored on the video tape 34, or these values may be increased or decreased as required. Through a set of different plug-in memories 32, the same video tape can be used to achieve differing levels of work for the user, thereby resulting in a more or less severe test and regime' for the user.

One use of this apparatus is to load the video tape player 35 with a cassette (or the CPU with a ROM program) depicting a race. In fact, the video tape 34 can be recorded in a race against time, a distance race, an obstacle race, or a race with professional racers. The race can be against one or many opponents. The race can, thereafter, be viewed through the video tape player 35 and the race can then be weighted to accommodate those who are just beginning an exercise program. As they progress, the race can be made more difficult. As a matter of choice, the race can be made more strenuous or faster than that experienced by the camera operator who actually records the video tape 34. An alternate source of video signals for the user is a stored set of prompts to the user which instructs the user to pedal for certain timed intervals at certain speeds against a fixed or modified drag. Such prompts preferably include characters written by the generator 38.

PULSE RATE DETECTION AND USE

One feature of this apparatus is the pulse sensor 40. It notes or observes the pulse rate. There is an empirical relationship between the power output at the exercise bicycle and pulse rate. It has been discovered that this empirical relationship requires testing at several levels. The following sequence has been found to be acceptable. The bicycle is operated for an initial warmup period of three minutes while the output is 25 watts. The output can be obtained by measuring the velocity and the setting on the drag brake. Power output is proportional to these two factors. In any case, it is operated for a period of three minutes at 25 watts power output. Then, the power output requirement is altered. This can be achieved by merely readjusting the drag brake. The rate is, therefore, increased to a plateau for 50 watts. The rate is again increased to another plateau for 75 watts. It is again increased to several plateaus, typically up to about 175 watts. The rate is increased in increments of 25 or 50 watts, and this occurs every three minutes. Each level is sustained typically for three minutes to permit the heart rate of the user to stabilize. The heart rate is measured during the last fifteen seconds of each work level. This procedure can be visualized where the heart rate is plotted against power output in watts. Ideally, more than three points are obtained, typically four or five measurements being sufficient. The plot is fitted to a straight line by using a least squares algoritm utilizing pulse rate as the ordinate. The other variable is power output. The plot obtained is extrapolated to the predicted maximum heart rate which is given by 220 minus the age of the user. This point of intersection determines the power output on that axis. This is an estimate of maximum power output of the user. This is typically in the range of about 175-250 watts, depending on the condition of the user, and other health related variables. Assume, for purposes of illustration, that the estimated working capacity of the individual is 205 watts. The maximum oxygen uptake factor is then given by the equation below:

$$V_m = 0.013 (W_m) + 0.18$$

Where
$V_m$ = oxygen uptake in liters/minute
$W_m$ = estimated working capacity in watts This value should normally be divided by the body weight in kilograms. For an example, where the estimated maximum capacity is 205 watts, and the user weights 70 kilograms, this yields a maximum value of oxygen uptake of about 2.85 liters/minute. Dividing by weight, one obtains 40.6 milliliters/kilogram/minute.

The foregoing example of measurements is reasonably reliable provided the plateaus of exercise permit the heart rate to stabilize. It will be appreciated that a change in work load does not produce an instantaneous change in heart rate. In light of this, each plateau must be prolonged sufficiently that the body of the user stabilizes at the elevated rate. It is desirable that the plateaus be at least about two minutes in length. They can be longer, but this makes the test entirely too long so that the cumulative body fatigue of the user becomes a factor. Ideally, a test lasting in the range of nine to twelve minutes is sufficient with three minute plateaus.

The foregoing description speaks of the calculations as though they were visually presented on a graph. In practice, the values required for such a plot are input to the CPU and stored in memory. On completion of the procedure, the CPU implements the curve fitting with an error reduction procedure to define a plot (visually speaking) and projects to determine the intercept with the predicted maximum heart rate (220 − age of user).

The steps of 25 watts after three minute intervals is preliminary to the procedure above. Due to its programmability, the present invention can be used to test for oxygen uptake using different parameters, namely, different steps. In that event, the constants will be different from those given in the linear equation above.

When the oxygen uptake test begins, the user is visually instructed to pedal the bicylce for a timed interval at a certain rate. When that interval ends, the drag is changed to force the user to exert more effort. The power output is monitored during use and the user is instructed to speed up if the power output sags. Each step is completed and then the CPU computes the final value of oxygen uptake. Needless to say, the user must input his age as a preliminary step.

This is a roughly calculated value which is fairly accurate as an expression of the physical fitness of the user. It can be obtained from the apparatus of FIG. 1 by providing the video tape 34 with the instructions for the user. Alternatively, ROM stored instructions may be used via the generator 38. In operation, the first plateau is achieved when the bicycle obtains an output of 25 watts. This level of output is obtained with a particular setting on the brake 21 and sustaining a particular speed. This level of output is obtained with a particular setting on the brake 21 and sustaining a particular speed. It is obtained for a measured interval, and this can be readily implemented by recording the video tape with instructions to the user to maintain that speed against that particular load for a specified interval. The power output is then stepped. This can be implemented again rather easily by altering the setting on the brake. Alternatively, it can be obtained by instructing the user to increase the pace. If the user does not achieve the required pace, this too can be measured, and suitable instructions can be flashed on the video monitor to the user. As an example, the user can be told to speed up the pedaling action.

There are handy ways to measure the power output of the bicycle. The force experienced on the crank is proportional to the load. Accordingly, the loading of the user on the crank is sensed by the strain gauge 25 and is transmitted or commutated for recovery. Power output is given by the simple multiplication of measured value and is, therefore, easily measured with transducers mounted on the exercise bicycle. Of course, other force measuring transducers may be used.

ALTERNATE FORMS OF APPARATUS

FIG. 1 discloses an alternate form of apparatus. The alternate form of apparatus utilizes a weighted bar 50. The bar supports weights at 51 and 52. The bar is raised and lowered relative to a particular track or supportive frame. The bar, in turn, supports a contact 53. The contact 53 is contacted against a linear slide resistor 54. Obviously, any standard rotary potentiometer can be used in lieu of the slide wire resistor. There needs only to be a simple mechanical means to convert the linear movement of the weight to the rotary movement of the potentiometer. The resistor 54 is provided with a bias voltage source 55. The slide wire resistor 54 is grounded. A suitable voltage level is picked off by the wiper 53. It is supplied to an amplifier 56 which, in turn, is input to the CPU 30 via a signal conditioner 58.

As the bar 50 is lifted in exercising, it generates a voltage which is indicative of the position of the bar. For instance, this would indicate when the bar is lifted above the guides 57 which support it. This also indicates the rate of upward movement. The rate can be obtained by observing the voltage wave form as a function of time. This wave form indicates position, and the rate of change of position is velocity. The time rate of change of velocity is acceleration. These factors can be obtained quite readily from the signal voltage from the amplifier 56 by taking the first and second derivatives of this signal. These values are obtained repetitively by the CPU on each sampling.

In similar fashion, the numeral 60 identifies a lever which connects with a handle 61. The handle 61 is grapsed by a user and rotates the lever 60. The lever 60 pivots around a pin or post 62. A slide wire resistor 63 is arranged in a segment of a circle around the pivot point 62. Again, a suitable battery (or equivalent) is incorporated at 64. The lever 60 supports a wiper arm 65. It forms an output voltage supplied through an amplifier 66 which, in turn, is input to the CPU via the signal conditioner 67.

The rotative apparatus can be impeded by placing weights on it. Alternatively, a friction drag brake of the sort shown at 21 can impede rotation. Other alternate forms of brake include disc, cone, drum, centrifugal and hydraulic brakes. Whatever the case, the resistance can be controlled so that the signal supplied from the apparatus is indicative of the position of the apparatus. It is similar to the signal from the weighted bar 50 discussed above. Both signals (after conditioning) are input to the CPU programmed conveniently to measure and calculate the work of the user. Moreover, either set of equipment can be used in conjunction with the video monitor 36 to instruct the user to perform a given exercise while mimicking the image shown on the video monitor 36. For instance, consider use of the rotative apparatus including the handle 61 for bicep exercise. By use of a video tape of a bicep exercise by an instructor depicting proper form and pacing, the user can exercise with the rotative apparatus including the lever 60 and the handle 61 to maintain synchronous movement with that shown on the video monitor 36. Moreover, the loading can be adjusted to meet a programmed pattern. For instance, the bicep exercise can be repeated for three or four movements with minimum loading. Then, audio signals obtained from the ROM or the audio track video tape 34 encode modifications of the drag experienced on the lever 60. This modification can be implemented quite easily through the drag brake 61. The drag brake 61 thus works against rotation of the lever arm. The video seen by the user is stored in ROM memory driving the generator 38. This alternate source of video instructs the user.

This example can be extended to movement of the weighted bar 50. That bar can be raised and lowered, and various and sundry exercises can be repeated through the use of the bar. Again, the monitor 36 can be installed to instruct the user by providing a video tape of an instructor. Pacing and form can be observed in the video tape. Moreover, the actual performance of the user can be observed with this equipment and various and sundry messages can be flashed on the video monitor instructing the user to speed up or to slow down. The messages may be very large to fill the screen; they may also be small at one side, or even flashed intermittenly for the user partially obscuring the filmed action.

The foregoing is directed to the preferred embodiment. The scope, however, is determined by the claims which follow.

I claim:

1. For use with an exercise device including a movable part and moved by exercise of an user input through an input means and retarded by an adjustable brake, and further including sensor means for detecting the rate of exercising on the exercise device by a user, the apparatus comprising:
   (a) means for receiving a specified exercise rate for a user;
   (b) comparator means for comparing the specified exercise rate from said receiving means with the exercise rate sensed by the sensor means on the exercise device;
   (c) a video monitor positioned to be viewed by the user;
   (d) video player means adapted to be loaded with a storage medium having a video storage track and a separable storage track;
   (e) means connecting a video signal output from said video player means to said video monitor to form a visual image for a user;
   (f) signal forming means responsive to said storage medium wherein a signal is recorded on the separable storage track, said signal forming means forming signals from said storage track applied to said receiving means to set an instantaneous specified exercise rate for the user responsive to the signal of said storage track; and
   (g) wherein said storage track signal varies said instantaneous specified exercise rate.

2. The apparatus of claim 1 wherein said video tape player means is adapted for playing a video tape having recorded thereon a bicycle ride to be shown to the user to enable the user to mimic the bicycle ride on the exercise bicycle; and wherein said sensor means forms a signal indicative of the velocity of the user on the exercise bicycle and said comparator means measures the user's velocity against the velocity of the recorded bicycle ride, and character generator means forms the an instruction visually instructing the user to match the velocity of the recorded ride.

3. The apparatus of claim 2 wherein said character generator means forms a signal instructing the user in characters readable by the user on said video monitor.

4. The apparatus of claim 2 wherein said signal forming means forms the signal instructing the user and the signal is supplied to a circuit means connected to an electromagnetically powered brake adjustment means connected to the brake on the exercise device to vary resistance of the exercise device to the user.

5. The apparatus of claim 4 wherein said brake adjustment means includes a solenoid to vary the setting of the brake.

6. The apparatus of claim 4 wherein said circuit means comprises a current amplifier means.

7. The apparatus of claim 6 wherein said output means comprises a means forming a setting voltage for said current amplifier means.

8. The apparatus of claim 1 wherein the exercise device is a stationary bicycle and including central processor means for calculating in real time the velocity of a user on the bicycle and forming a signal for use with said comparator means.

9. The apparatus of claim 1 for testing the physical fitness of a user further comprising:
   (a) power sensor means for measuring the rate of power output by a user at said exercise device;
   (b) pulse sensor means for obtaining the pulse rate of a user;
   (c) time dependent means instructing a user to operate said exercise device for a timed interval at a specified rate of power output; and
   (d) calculating means provided with an input of the pulse rate from said pulse rate sensor means and also provided with an input from said power sensor means, said calculating means forming an output signal indicative of the rate of oxygen uptake of the user.

10. The apparatus of claim 9 including:
   (a) means for adjusting said exercise device to require power output by the user at an increased rate; and
   (b) timer means for holding for a specified interval the required output from said exercise device.

11. The apparatus of claim 10 wherein:
(a) said exercise device is an exercise bicycle having;
  (1) a rotatable member;
  (2) an adjustable brake acting against said rotatable member;
  (3) electromagnetic means connected to said brake for operating said brake adjustably to vary the braking force thereof; and
  (4) pedals operated by the user at a specified rate for rotating said rotatable member;
(b) said power sensor means forms a signal indicative of the rate of power generated by the user in operation; and
(c) means forming an input signal to said video monitor for forming an instruction visually directed to the user to instruct the user on the rate of speed of the user in pedalling said exercise bicycle to form a desired power output as indicated by said power sensor means.

12. The apparatus of claim 11 wherein said exercise bicycle electromagnetic means comprises an electrically operated drag brake adjustably set by the signal applied thereto; further including an input means adapted to receive a signal storage means for inputting a signal to said input means; and
means for forming a control signal from the input signal and applying the control signal to said electrically operated drag brake.

13. The apparatus of claim 1 including central processor means which comprises said comparator means, and memory means for storing a program of instructions for said central processor means, said memory means being connected with said central processor means by connectable means enabling changing of said memory means.

14. The apparatus of claim 13 including multiple alternate memory means selectively switched in and out by said connectable means wherein said alternate memory means provide alternate instructions for operation of said central processor means.

15. The apparatus of claim 14 wherein said memory means comprises two separate memory means, one of said memory means providing a program of instruction which specifies sequences of operation for said comparator means; and the other of said memory means which stores a sequence of weighting values to vary the specified exercise rate desired for the exercise bicycle.

16. The apparatus of claim 13 wherein said memory modular stores modified values of exercise rates therein.

* * * * *